(12) United States Patent
Akao et al.

(10) Patent No.: US 11,223,077 B2
(45) Date of Patent: Jan. 11, 2022

(54) POWER SUPPLY UNIT FOR AEROSOL INHALER, METHOD OF DIAGNOSING STATE OF POWER SUPPLY OF AEROSOL INHALER, AND PROGRAM FOR DIAGNOSING STATE OF POWER SUPPLY OF AEROSOL INHALER

(71) Applicant: Japan Tobacco Inc., Tokyo (JP)

(72) Inventors: Takeshi Akao, Tokyo (JP); Manabu Yamada, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 0 days.

(21) Appl. No.: 16/726,942

(22) Filed: Dec. 26, 2019

(65) Prior Publication Data

US 2020/0212516 A1 Jul. 2, 2020

(30) Foreign Application Priority Data

Dec. 27, 2018 (JP) .............................. JP2018-244968

(51) Int. Cl.
  *H01M 10/48* (2006.01)
  *A24F 40/90* (2020.01)
  *A24B 15/167* (2020.01)
  *A61M 15/06* (2006.01)

(52) U.S. Cl.
  CPC ......... *H01M 10/488* (2013.01); *A24B 15/167* (2016.11); *A24F 40/90* (2020.01); *A61M 15/06* (2013.01)

(58) Field of Classification Search
  None
  See application file for complete search history.

(56) References Cited

U.S. PATENT DOCUMENTS

| 9,839,238 | B2 * | 12/2017 | Worm ..................... A24F 40/50 |
| 2010/0194398 | A1 | 8/2010 | Kawasumi et al. |
| 2017/0027234 | A1 | 2/2017 | Farine et al. |
| 2018/0196107 | A1 | 7/2018 | Fleischer et al. |

FOREIGN PATENT DOCUMENTS

| CA | 3 054 273 A1 | 9/2018 |
| CN | 107121639 A | 9/2017 |
| CN | 107923944 A | 4/2018 |
| JP | 2017-514463 A | 6/2017 |

(Continued)

OTHER PUBLICATIONS

Notification of Reasons for Refusal received for Japanese Patent Application No. 2018-244968, dated May 14, 2019, 8 pages including English Translation.

(Continued)

*Primary Examiner* — Dennis R Cordray
(74) *Attorney, Agent, or Firm* — Xsensus LLP

(57) ABSTRACT

A power supply unit for an aerosol inhaler includes: a power supply able to discharge power to a load for generating an aerosol from an aerosol source; and a control unit configured to perform a plurality of types of processes for diagnosing a state of the power supply. The plurality of types of processes are different in at least one of time which is required to obtain a result of diagnosis and information which is used to obtain a result of diagnosis.

13 Claims, 8 Drawing Sheets

(56) References Cited

FOREIGN PATENT DOCUMENTS

WO      2015/165747 A1    11/2015
WO      2018/163261 A1    9/2018

OTHER PUBLICATIONS

English Translation of Written Amendment received for Japanese Patent Application No. 2018-244968, dated Jul. 5, 2019, 5 pages.
Decision to Grant a Patent received for Japanese Patent Application No. 2018-244968, dated Jul. 30, 2019, 5 pages including English Translation.
Eurasian Notification issued Mar. 20, 2020 in Eurasian Application No. 201992847/26.
Search Report dated Jun. 2, 2020 in European Patent Application No. 19219827.3, 5 pages.
Operating Manual Dicodes: "2395 / 2395T Bedienungsanleitung", Sep. 21, 2016 (Sep. 21, 2016), pp. 1-14, XP055693155, dicodes website Retrieved from the Internet: URL:https://www.dicodes-mods.de/dicodes-2395.html.
Office Action dated Feb. 9, 2021, in corresponding Chinese patent Application No. 201911376049.6, 17 pages.

\* cited by examiner

US 11,223,077 B2

POWER SUPPLY UNIT FOR AEROSOL INHALER, METHOD OF DIAGNOSING STATE OF POWER SUPPLY OF AEROSOL INHALER, AND PROGRAM FOR DIAGNOSING STATE OF POWER SUPPLY OF AEROSOL INHALER

CROSS-REFERENCE TO RELATED APPLICATIONS

This application is based upon and claims the benefit of priority from prior Japanese patent application No. 2018-244968, filed on Dec. 27, 2018, the entire contents of which are incorporated herein by reference.

TECHNICAL FIELD

The present invention relates to a power supply unit for an aerosol inhaler, a method of diagnosing a state of a power supply of an aerosol inhaler, and a program for diagnosing a state of a power supply of an aerosol inhaler.

BACKGROUND ART

An aerosol inhaler is known which includes an aerosol generation source, a load for generating an aerosol from the aerosol generation source, a power supply able to discharge power to the load, and a control unit for controlling the power supply (for example, see Patent Literature 1).

The device disclosed in Patent Literature 1 measures the voltage between the terminals of an electric energy supply source in the course of use, and monitors whether the corresponding voltage is lower than a threshold for the voltage at an arbitrary time point by comparing it with the threshold. However, by only measuring voltage drop, it is not possible to determine whether it is just required to recharge the battery, or deterioration of the battery has progressed so much that replacement is required. For this reason, the aerosol generating device disclosed in Patent Literature 1 tracks voltage drop from the status of the usage record, and issues a signal when battery replacement is required.

[Patent Literature 1] JP-T-2017-514463

Deterioration of a battery progresses due to various causes, and the degree of progress of deterioration depends on the use environment and use condition of the device. Therefore, even though a method of diagnosing the state of a battery disclosed in Patent Literature 1 is used, it is difficult to improve the accuracy of diagnosis of the state of a battery by only the single method. Also, in order to improve the safety of the device, it is desirable to diagnose abnormalities of a power supply, in addition to the degree of progress of deterioration of a battery. For this reason, it is desired to be able to diagnose existence or non-existence of deterioration and the like by a plurality of methods. In Patent Literature 1, it is not disclosed that diagnosis of the state of a battery is performed by a plurality of methods.

An object of the present invention is to provide a power supply unit for an aerosol inhaler, a method of diagnosing a state of a power supply of an aerosol inhaler, and a program for diagnosing a state of a power supply of an aerosol inhaler, capable of performing diagnosis of the state of the power supply with high accuracy.

SUMMARY OF INVENTION

According to an aspect of the invention, there is provided a power supply unit for an aerosol inhaler, the power supply unit comprising: a power supply able to discharge power to a load for generating an aerosol from an aerosol source; and a control unit configured to perform a plurality of types of processes for diagnosing a state of the power supply, wherein the plurality of types of processes are different in at least one of time which is required to obtain a result of diagnosis and information which is used to obtain a result of diagnosis.

DESCRIPTION OF EMBODIMENTS

Figure 1:
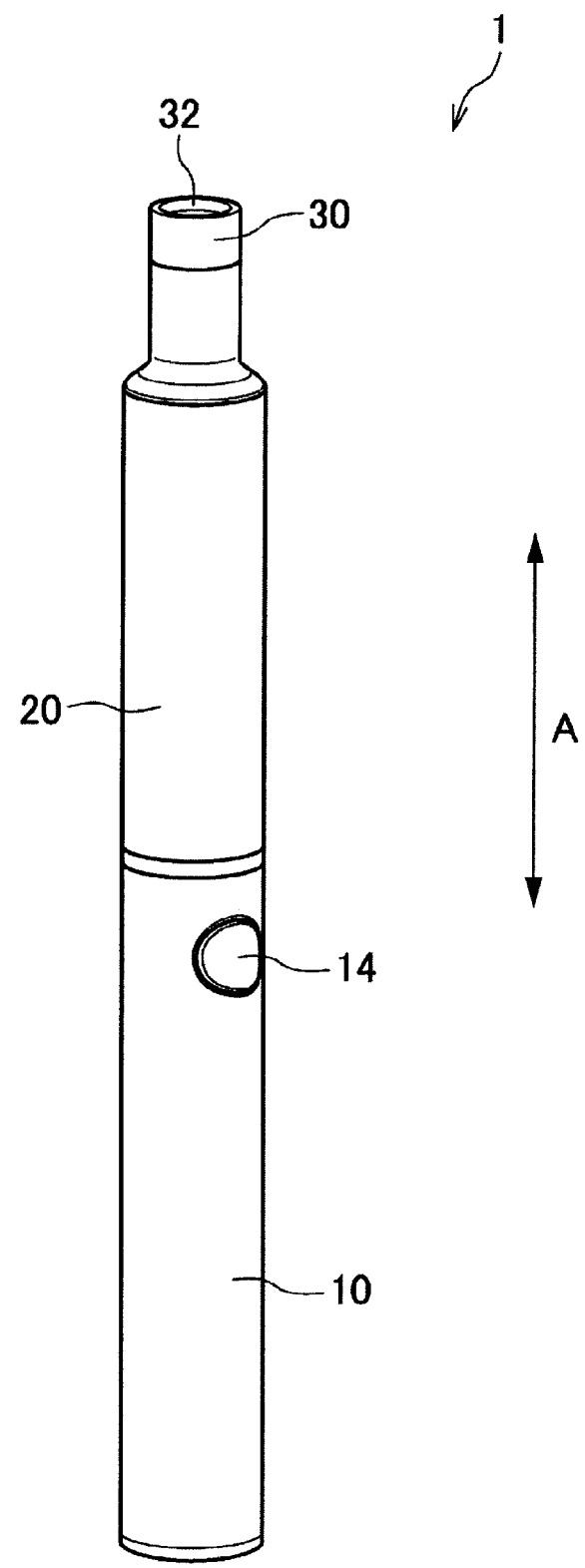
FIG. 1 is a perspective view of an aerosol inhaler equipped with a power supply unit of an embodiment of the present invention.
Figure 2:
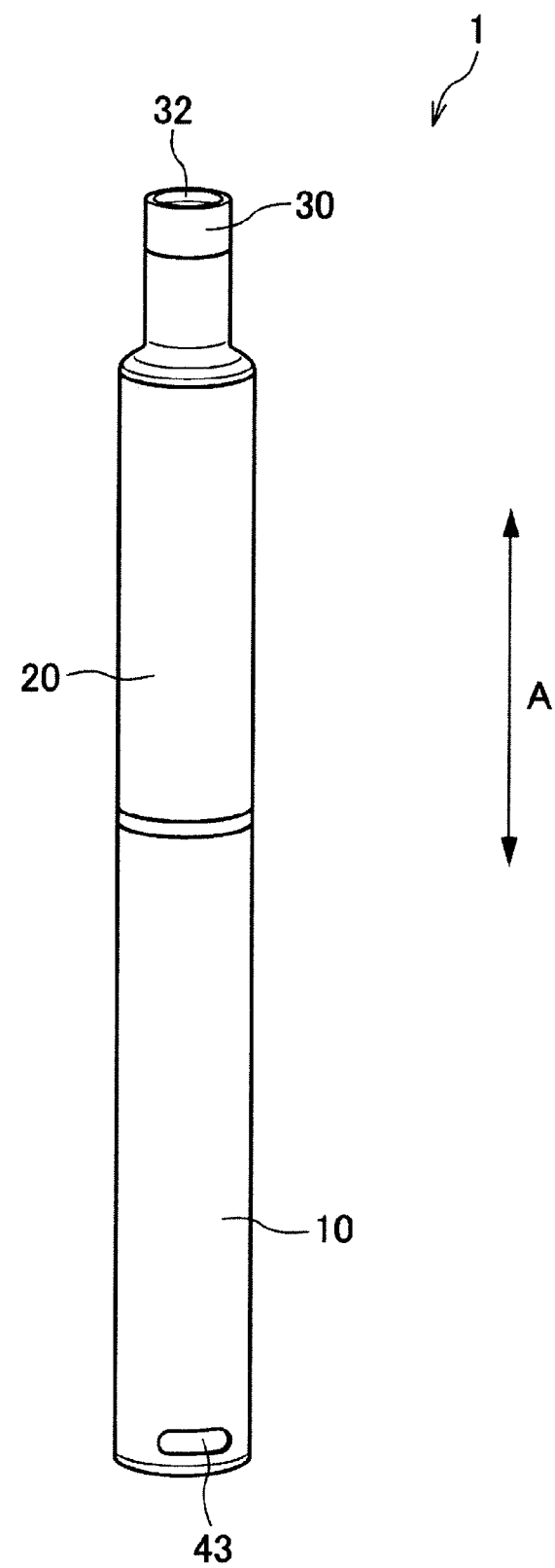
FIG. 2 is another perspective view of the aerosol inhaler of FIG. 1.

Hereinafter, a power supply unit for an aerosol inhaler according to an embodiment of the present invention will be described. First of all, an aerosol inhaler equipped with the power supply unit will be described with reference to FIG. 1 and FIG. 2.

(Aerosol Inhaler)

An aerosol inhaler 1 is a device for inhaling an aerosol containing a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10. The second cartridge 30 can be attached to and detached from the first cartridge 20. In other words, the first cartridge 20 and the second cartridge 30 can be individually replaced.

(Power Supply Unit)

The power supply unit 10 of the present embodiment includes a power supply 12, a charging IC 55, an MCU (Micro Controller Unit) 50, a switch 19, a pressure sensor 13, a voltage sensor 16, a temperature sensor 17, various sensors, and so on in a cylindrical power supply unit case 11, as shown in FIG. 3, FIG. 4, FIG. 5, and FIG. 6. The power supply 12 is a chargeable secondary battery, an electric double-layer capacitor, or the like, and is preferably a lithium-ion battery. The following description will be made on the assumption that the power supply 12 is a lithium-ion battery.

On a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20.

Further, on a part of the top surface of the top part 11a in the vicinity of the discharging terminal 41, an air supply part 42 for supplying air to the load 21 of the first cartridge 20 is provided.

On a bottom part 11b of the power supply unit case 11 positioned on the other end side in the longitudinal direction A (the opposite side to the first cartridge 20), a charging terminal 43 able to be electrically connected to an external power supply 60 (see FIG. 6) capable of charging the power supply 12 is provided. The charging terminal 43 is provided on the side surface of the bottom part 11b, such that, for example, at least one of USB terminals, micro USB terminals, and lightning terminals can be connected thereto.

However, the charging terminal 43 may be a power receiving part able to receive power from the external power supply 60 in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from the external power supply 60 without any contact point. As another example, the charging terminal 43 may be configured such that at least one of USB terminals, micro USB terminals, and lightning terminals can be connected thereto and the above-mentioned power receiving part is included therein.

On the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line of the power supply unit 10 in the longitudinal direction A. The operation unit 14 is composed of a button type switch, a touch panel, or the like. In the vicinity of the operation unit 14, an inhalation sensor 15 for detecting puff actions is provided.

The charging IC 55 is disposed close to the charging terminal 43, and performs control on charging of the power supply 12 with power which is input from the charging terminal 43. The charging IC 55 includes a converter for converting direct current, which is applied from an inverter 61 or the like (see FIG. 6) provided for converting alternating current into direct current on a charging cable which is connected to the charging terminal 43, into direct current having a different magnitude, a voltmeter, an ammeter, a processor, and so on.

Figure 5:
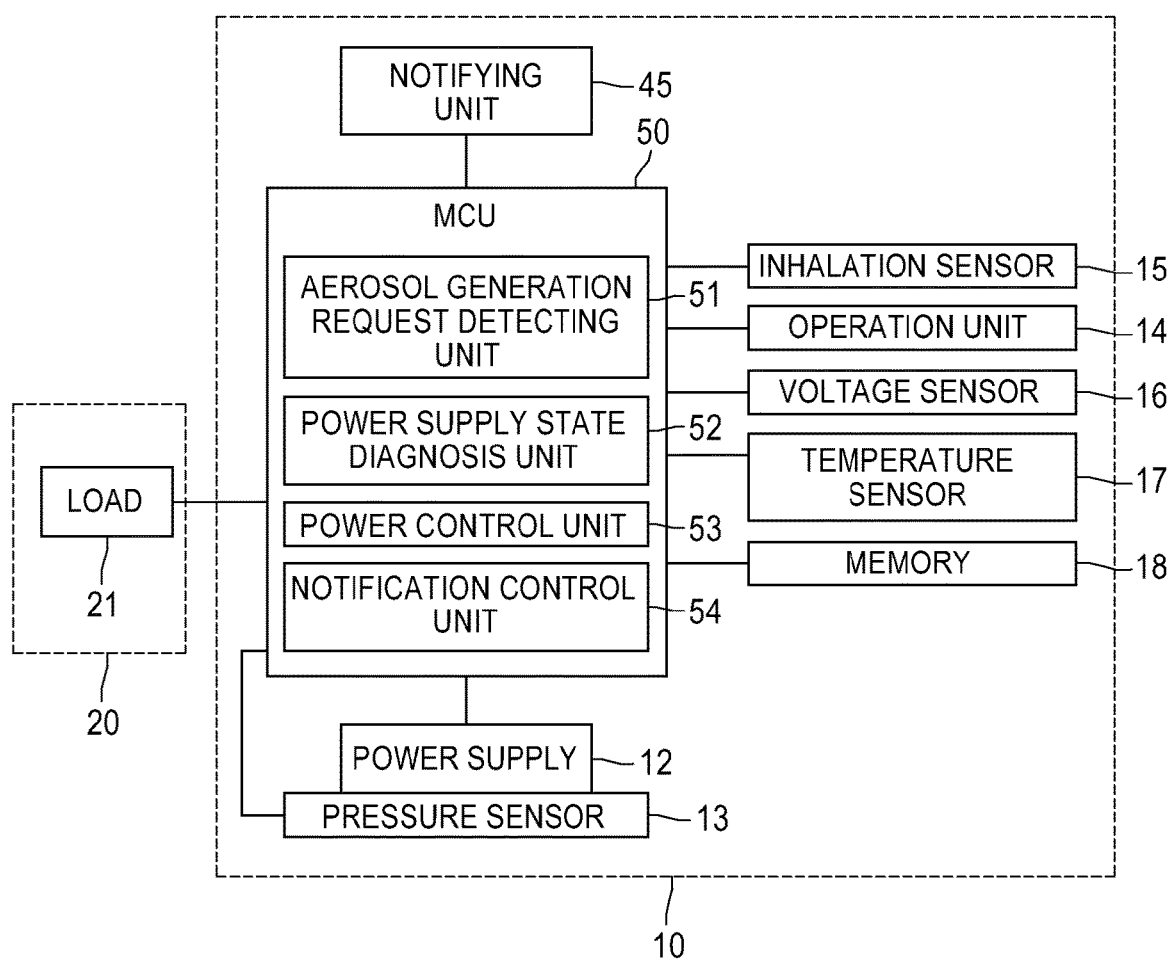
FIG. 5 is a block diagram illustrating the main part configuration of the power supply unit in the aerosol inhaler of FIG. 1.

The MCU 50 are connected to various sensor devices, such as the pressure sensor 13 attached to the power supply 12 in order to measure the amount of swelling of the power supply 12 (swelling which is caused by deterioration of the power supply 12), the inhalation sensor 15 for detecting puff (inhaling) actions, a voltage sensor 16 for measuring the power-supply voltage of the power supply 12, and a temperature sensor 17 for measuring the temperature of the power supply 12, the operation unit 14, a notifying unit 45 (to be described below), and a memory 18 for storing the number of puff actions, the time for which power has been applied to the load 21, as shown in FIG. 5, and performs a variety of control on the aerosol inhaler 1. Specifically, the MCU 50 is configured mainly with a processor, and further includes storage media such as a RAM (Random Access Memory) necessary for the operation of the processor and a ROM (Read Only Memory) for storing a variety of information. In this specification, the processor is more specifically an electric circuit configured by combining circuit elements such as semiconductor elements.

Also, in the power supply unit case 11, an air intake (not shown in the drawings) for taking in air is formed. However, the air intake may be formed around the operation unit 14, or may be formed around the charging terminal 43.

(First Cartridge)

Figure 3:
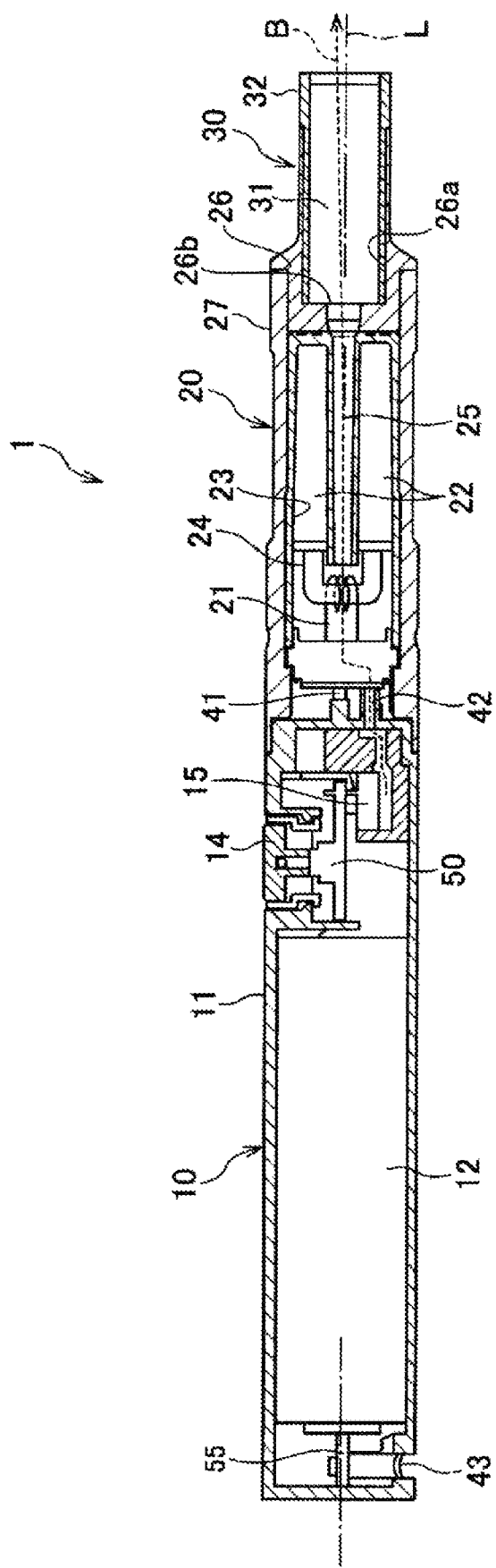
FIG. 3 is a cross-sectional view of the aerosol inhaler of FIG. 1.
Figure 4:
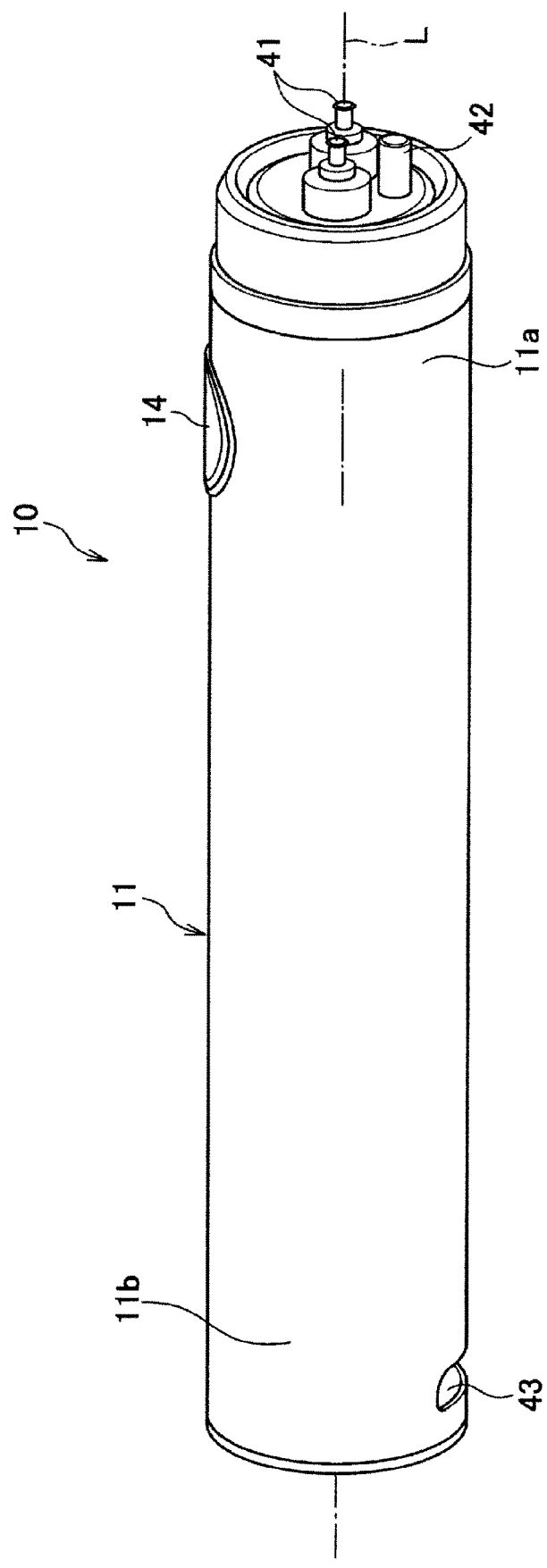
FIG. 4 is a perspective view of the power supply unit in the aerosol inhaler of FIG. 1.

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, and an end cap 26 for storing a part of the second cartridge 30, inside a cylindrical cartridge case 27.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 from the reservoir 23 toward the load 21 using capillarity, and is configured with, for example, glass fiber, a porous ceramic, or the like.

The load 21 atomizes the aerosol source 22 without combustion by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator. Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

(Second Cartridge)

The second cartridge 30 holds a flavor source 31. The end part of the second cartridge 30 on the first cartridge (20) side is stored in the cartridge storage part 26a provided in the end cap 26 of the first cartridge 20, so as to be able to be removed. The end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with a plant (such as mint or a herbal medicine, or a herb) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 constitute an aerosol generation source for generating an aerosol.

The aerosol generation source in the aerosol inhaler 1 is a part which the user can replace to use. For this part, for example, one first cartridge 20 and one or more (for example, five) second cartridges 30 can be provided as one set to the user.

The configuration of an aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

For an aerosol inhaler 1 including an aerosol generation source configured by integrally forming an aerosol source 22 and a flavor source 31, for example, one or more (for example, 20) aerosol generation sources may be provided as one set to the user.

In the case of an aerosol inhaler 1 including only an aerosol source 22 as an aerosol generation source, for example, one or more (for example, 20) aerosol generation sources may be provided as one set to the user.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, a notifying unit 45 for notifying a variety of information is provided (see FIG. 5). The notifying unit 45 may be configured with a light emitting element, or may be configured with a vibrating element, or may be configured with a sound output element. The notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by a light emitting element such as an LED to pass through.

(Electric Circuit)

Now, the details of the electric circuit of the power supply unit 10 will be described with reference to FIG. 6.

The power supply unit 10 includes the power supply 12, the voltage sensor 16 for measuring power-supply voltage $V_{Batt}$ which is the voltage of the power supply 12, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the MCU 50 which is connected between the positive electrode side of the power supply 12 and the positive electrode side discharging terminal 41a and between the negative electrode side of the power supply 12 and the negative electrode side discharging terminal 41b, the charging IC 55 which is disposed on the power transmission path between the charging terminal 43 and the power supply 12, and a switch 19 which is disposed on the power transmission path between the power supply 12 and the discharging terminal 41.

The switch 19 is configured with, for example, a semiconductor element such as a MOSFET, and is opened and closed by control of the MCU 50.

In the power-supply voltage $V_{Batt}$ which is measured by the voltage sensor 16 in a state where the charging IC 55 is not connected to the inverter 61, closed circuit voltage CCV which is the voltage of the power supply 12 in a state where the load 21 is connected to the discharging terminal 41 and the switch 19 is closed, and open circuit voltage OCV which is the voltage of the power supply 12 in a state where the load 21 is connected to the discharging terminal 41 and the switch 19 is open are included. The power-supply voltage $V_{Batt}$ measured by the voltage sensor 16 is transmitted to the MCU 50.

Figure 6:
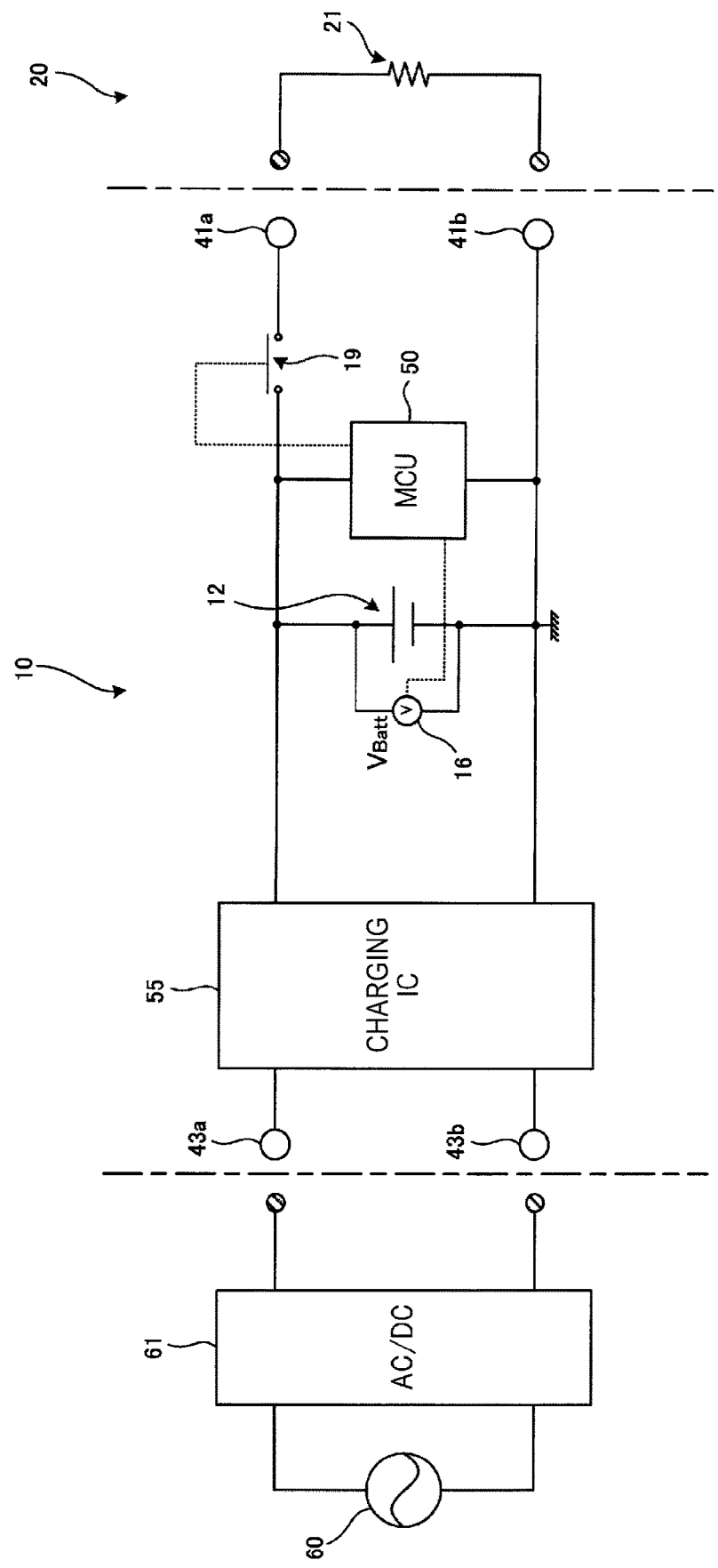
FIG. 6 is a schematic diagram illustrating the circuit configuration of the power supply unit in the aerosol inhaler of FIG. 1.

In the electric circuit of the power supply unit 10 shown in FIG. 6, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

(MCU)

Now, the configuration of the MCU 50 will be described in more detail.

As shown in FIG. 5, the MCU 50 includes an aerosol generation request detecting unit 51, a power supply state diagnosis unit 52, a power control unit 53, and a notification control unit 54 as functional blocks which the processor can implement by executing a program stored in the ROM.

The aerosol generation request detecting unit 51 detects a request for aerosol generation based on the output result of the inhalation sensor 15. The inhalation sensor 15 is configured to output the value of a variation in the pressure in the power supply unit 10 (the internal pressure) caused by inhalation of the user through the inhalation port 32. The inhalation sensor 15 is, for example, a pressure sensor for outputting an output value (for example, a voltage value or a current value) according to the internal pressure which varies according to the flow rate of air which is sucked from the intake (not shown in the drawings) toward the inhalation port 32 (i.e. puff actions of the user). The inhalation sensor 15 may be configured with a capacitor microphone or the like.

The power supply state diagnosis unit 52 diagnoses the state of the power supply 12. Specifically, the power supply state diagnosis unit 52 diagnoses whether the power supply 12 is in a deteriorated state in which deterioration has progressed to a predetermined state, or diagnoses whether the power supply 12 is in a broken state, using information such as the power-supply voltage $V_{Batt}$ which is an electric physical quantity which is measured by the voltage sensor 16, the temperature of the power supply 12 which is a non-electric physical quantity which is measured by the temperature sensor 17, and the value of pressure which is a non-electric physical quantity which is measured by the pressure sensor 13. As an example of the state in which deterioration of the power supply has progressed to the predetermined state and which is referred to in this specification, a state in which the state of heath (SOH) which is a numerical index representing the state of deterioration of the power supply 12 is 50% or less can be taken. The power supply state diagnosis unit 52 diagnoses the state of the power supply 12 in various aspects by individually performing a plurality of types of diagnosis processes. The details of this diagnosis processes will be described below.

By the way, it should be noted that both of the physical quantities measured by the voltage sensor 16 and the temperature sensor 17 are inputted as signals to the MCU 50.

The notification control unit 54 controls the notifying unit 45 to notify a variety of information. For example, the notification control unit 54 controls the notifying unit 45, in response to detection of the timing to replace the second cartridge 30, to notify the timing to replace the second cartridge 30. The notification control unit 54 detects and notifies a timing to replace the second cartridge 30, based on the cumulative number of puff actions and the cumulative time for which power has been supplied to the load 21, stored in the memory 18. The notification control unit 54 is not limited to notification of the timing to replace the second cartridge 30, and may notify the timing to replace the first cartridge 20, the timing to replace the power supply 12, the timing to charge the power supply 12, and so on.

In the state where one unused second cartridge 30 is set, if a predetermined number of puff actions are performed, or if the cumulative time for which power has been applied to the load 21 due to puff actions reaches a predetermined value (for example, 120 seconds), the notification control unit 54 determines that the second cartridge 30 is used up (i.e. the remaining amount is zero or the second cartridge is empty), and notifies the timing to replace the second cartridge 30.

Also, in the case of determining that all of the second cartridges 30 included in one set are used up, the notification control unit 54 may determine that one first cartridge 20 included in the single set is used up (i.e. the remaining amount is zero or the first cartridge is empty), and notify the timing to replace the first cartridge 20.

The power control unit 53 controls discharging of the power supply 12 through the discharging terminal 41 by switching on and off the switch 19, if the aerosol generation request detecting unit 51 detects the request for aerosol generation.

The power control unit 53 performs control such that the amount of aerosol which is generated by atomizing the aerosol source by the load 21 falls in a desired range, i.e. such that power or the amount of power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

After supply of power to the load 21 starts in order to generate an aerosol, if a predetermined period passes, the power control unit 53 stops supply of power from the power supply 12 to the load 21. In other words, even while the user is actually performing a puff action, if the puff period exceeds a certain period, the power control unit 53 stops supply of power from the power supply 12 to the load 21. The certain period is determined to suppress variation in user's puff period.

By control of the power control unit 53, the current which flows in the load 21 during one puff action becomes substantially a constant value which is determined according to substantially constant effective voltage which is supplied to the load 21 by PWM control, and the resistance values of the discharging terminal 41 and the load 21. In the aerosol inhaler 1 of the present embodiment, when the user inhales an aerosol using one unused second cartridge 30, the cumulative time for which power can be supplied to the load 21 is controlled to a maximum of, for example, 120 seconds. Therefore, it is possible to obtain the maximum amount of power required to empty (use up) one second cartridge 30.

(Power Supply State Diagnosis Process)

In the present embodiment, the plurality of types of diagnosis processes which the power supply state diagnosis unit 52 performs include five types of diagnosis processes, i.e. a first diagnosis process, a second diagnosis process, a third diagnosis process, a fourth diagnosis process, and a fifth diagnosis process.

Each of the first diagnosis process, the second diagnosis process, the third diagnosis process, and the fourth diagnosis process is a process for diagnosing whether the power supply 12 has deteriorated due to a factor such as repetitive charging and discharging, leaving the power supply in the fully charged state or the discharge cutoff state, or environmental temperature.

The fifth diagnosis process is a process for diagnosing whether the power supply 12 is in a broken state caused by a factor such as foreign matter inclusion, impact, or a short circuit in an external circuit. Hereinafter, the individual diagnosis processes will be described.

(First Diagnosis Process)

The first diagnosis process is a process of diagnosing whether the power supply 12 is in the deteriorated state, based on change in the discharge characteristic of the power supply 12.

Figure 7:
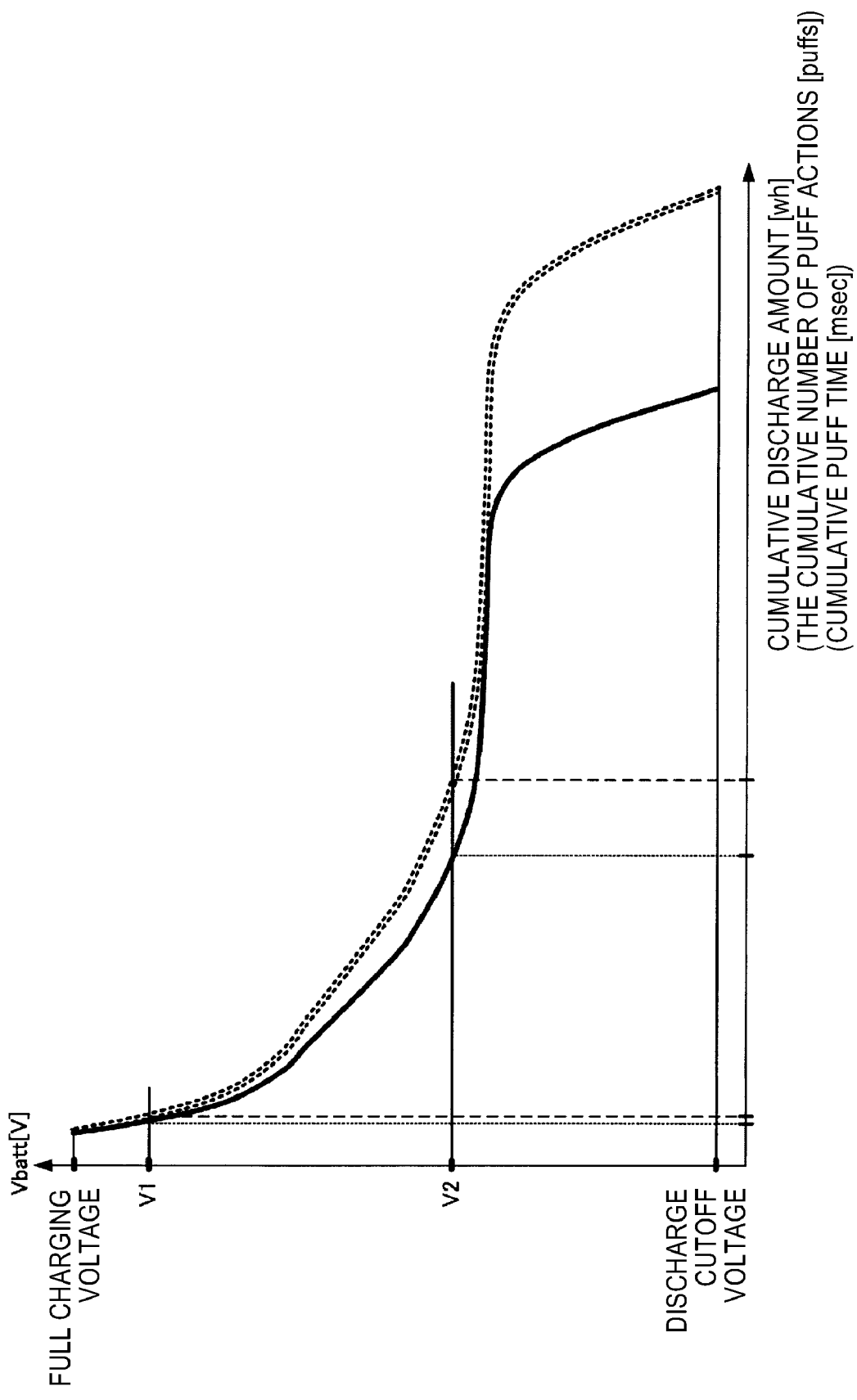
FIG. 7 is a view illustrating examples of the discharge characteristics of a power supply which is brand new and a power supply which has deteriorated, in the aerosol inhaler of FIG. 1.

FIG. 7 is a view illustrating examples of the discharge characteristic of the power supply 12 when it is brand new and the discharge characteristic of the power supply 12 when it has deteriorated. The vertical axis of FIG. 7 represents the power-supply voltage $V_{Batt}$ (open circuit voltage OCV or closed circuit voltage CCV) of the power supply 12. The horizontal axis of FIG. 7 represents the integrated value of the amount of discharge of the power supply 12. A curve shown by a broken line in FIG. 7 represents the discharge characteristic of the power supply 12 when it is brand new. A curve shown by a solid line in FIG. 7 represents the discharge characteristic of the power supply 12 when it has deteriorated.

As shown in FIG. 7, as deterioration of the power supply 12 progresses, even though the power-supply voltage $V_{Batt}$ is constant, the cumulative discharge amount decreases. A large difference in the cumulative discharge amount occurs in a region just before a so-called plateau region in which the drop in the power-supply voltage per unit discharge amount is gentle. In the first diagnosis process, the power supply state diagnosis unit 52 monitors the cumulative discharge amount of the power supply 12 in the region just before the plateau region of the power supply 12 when it is brand new.

Specifically, the power supply state diagnosis unit 52 sets the voltage corresponding to the cumulative discharge amount just before the plateau region of the discharge characteristic of the power supply 12 when it is brand new, as a threshold voltage V2, and sets a threshold voltage V1 higher than the threshold voltage V2 and lower than the full charging voltage.

The power supply state diagnosis unit 52 determines whether the cumulative discharge amount of the power supply 12 in the period from when the power-supply voltage $V_{Batt}$ which is measured by the voltage sensor 16 becomes the threshold voltage V1 to when the value of the power-supply voltage $V_{Batt}$ which is measured by the voltage sensor 16 reaches the threshold voltage V2 exceeds a predetermined threshold. The power supply state diagnosis unit 52 diagnoses that the power supply 12 is in a state in which the power supply keeps such performance that replacement is not required (in other words, the power supply is not in the deteriorated state in which deterioration has progressed to the predetermined state) if the cumulative discharge amount exceeds the threshold, and diagnoses that the power supply 12 is in a state in which deterioration has progressed so much that replacement is required (in other words, the power supply is in the deteriorated state in which deterioration has progressed to the predetermined state) if the cumulative discharge amount is equal to or smaller than the threshold.

However, the power supply state diagnosis unit 52 may use the cumulative number of puff actions which are detected in the period when the power-supply voltage $V_{Batt}$ is between the threshold voltage V1 and the threshold voltage V2, the cumulative time of the puff actions which are detected in the corresponding period, the cumulative power supply time for which power is supplied to the load 21 in the corresponding period, and so on, instead of the cumulative discharge amount of the power supply 12 in the corresponding period. If power or the amount of power which is supplied to the load 21 is controlled so as to fall in a certain range by the PWM control or the PFM control described above, it is possible to diagnose the state of the power supply 12 by only such a parameter which can be easily detected.

As described above, in the first diagnosis process, the above-mentioned period required to diagnose whether the power supply 12 is in the deteriorated state is determined according to the power-supply voltage $V_{Batt}$ which is measured by the voltage sensor 16. Therefore, in the first diagnosis process, the power-supply voltage $V_{Batt}$ which is measured by the voltage sensor 16 becomes one of information which is used to diagnose the state of the power supply 12.

Also, in the first diagnosis process, in order to obtain the result of the diagnosis on whether the power supply 12 is in the deteriorated state, a long period from when the power-supply voltage $V_{Batt}$ becomes the threshold voltage V1 to when the power-supply voltage reaches the threshold voltage V2 is required. If it is defined that the number of times of aerosol generation which is performed by performing discharging to the load 21 according to one puff action is one, the above-mentioned period has, for example, such a length that it is possible to perform aerosol generation several times.

(Second Diagnosis Process)

The second diagnosis process is a process of diagnosing whether the power supply 12 is in the deteriorated state, based on the amount of swelling of the power supply 12. As deterioration of the power supply 12 progresses, the power supply swells due to gas which is generated by decomposition of the electrolytic solution and an active material in the power supply 12, as compared to when the power supply is brand new. For this reason, it becomes possible to diagnose whether the power supply 12 has deteriorated, based on the amount of swelling. Specifically, the power supply state diagnosis unit 52 acquires the output signal of the pressure sensor 13, at a timing such as the timing when charging of the power supply 12 is completed by the charging IC 55 or the timing when the power-supply voltage $V_{Batt}$ reaches the discharge cutoff voltage, every charging and discharging cycle, or every two or more charging and discharging cycles.

In the ROM of the MCU 50, the output signal of the pressure sensor 13 when the power supply 12 is brand new is stored as a reference value in advance. In the case where a value obtained by subtracting the reference value from the output signal of the pressure sensor 13 acquired at the above-mentioned timing is equal to or larger than a predetermined value (i.e. in the case where the amount of swelling of the power supply 12 is large), the power supply state diagnosis unit 52 diagnoses that the power supply 12 is in a deteriorated state in which deterioration has progressed more than the predetermined state; whereas in the case where the value obtained by the subtraction is smaller than the predetermined value (i.e. in the case where the amount of swelling of the power supply 12 is small), the power supply state diagnosis unit diagnoses that the power supply 12 is not in the deteriorated state.

In the second diagnosis process, the output signal of the pressure sensor 13 becomes information which is used to diagnose the state of the power supply 12. Also, in the second diagnosis process, in order to obtain the result of the diagnosis on whether the power supply 12 is in the deteriorated state, a time longer than the time required in the first diagnosis process to obtain the diagnosis result, such as one charging and discharging cycle, or two or more charging and discharging cycles, is required.

(Third Diagnosis Process)

The third diagnosis process is a process of diagnosing whether the power supply 12 is in the deteriorated state, based on the internal resistance of the power supply 12. As deterioration of the power supply 12 progresses, the internal resistance of the power supply 12 increases. In the third diagnosis process, by monitoring change of the internal resistance, whether the power supply 12 is in the deteriorated state is diagnosed.

The power supply state diagnosis unit 52 sequentially acquires the open circuit voltage OCV of the power supply 12 and the closed circuit voltage CCV of the power supply 12, for example, in a period from when a puff action is detected to when aerosol generation according to the puff action starts, and calculates the internal resistance of the power supply 12 based on the acquired open circuit voltage OCV and the acquired closed circuit voltage CCV. Then, in the case where an internal resistance difference which is obtained by subtracting the internal resistance of the power supply 12 when it is brand new from the calculated internal resistance exceeds a predetermined resistance threshold, the power supply state diagnosis unit 52 diagnoses that the power supply 12 is in the deteriorated state in which deterioration has progressed more than the predetermined state; whereas in the case where the internal resistance difference is equal to or smaller than the resistance threshold, the power supply state diagnosis unit diagnoses that the power supply 12 is not in the deteriorated state.

Figure 8:
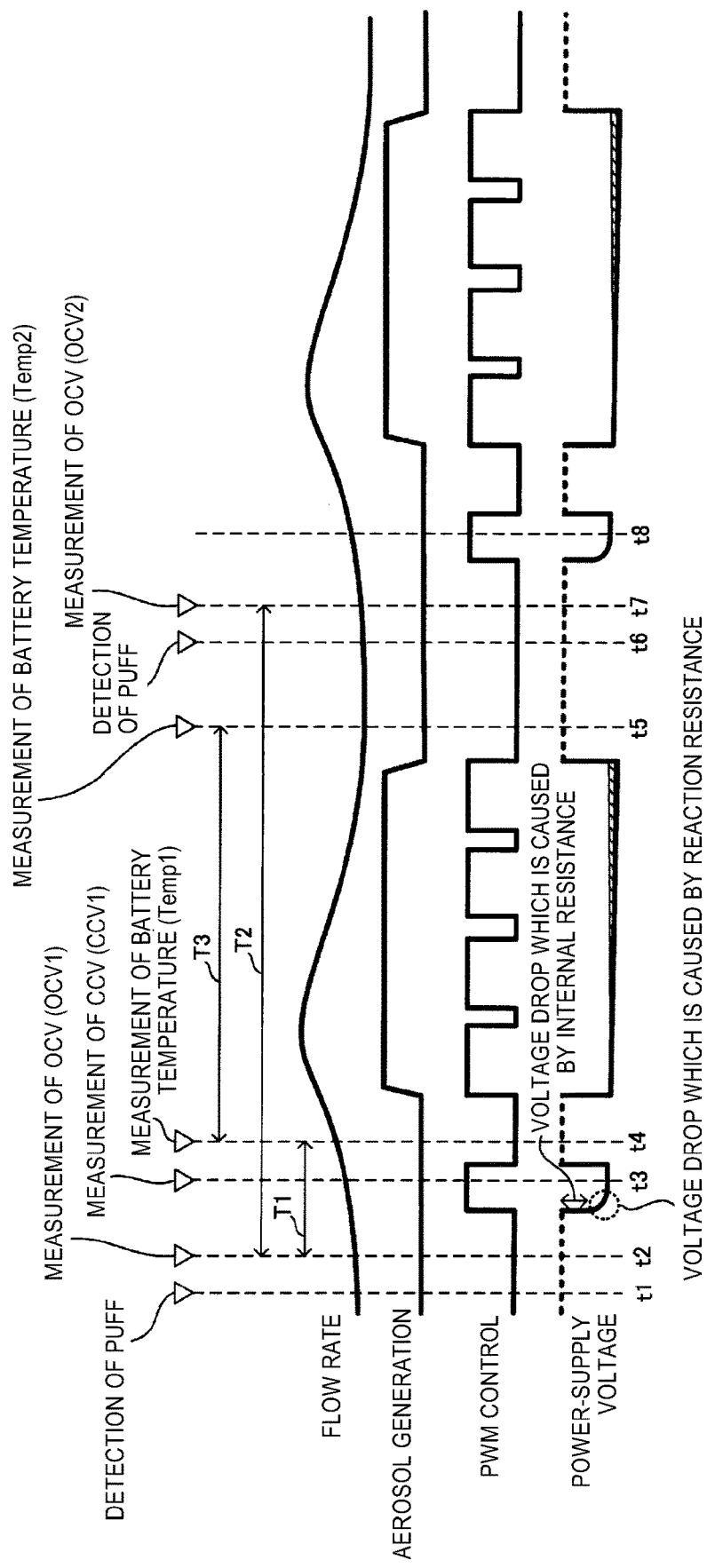
FIG. 8 is a timing chart illustrating when the aerosol inhaler of FIG. 1 performs aerosol generation according to puff actions.

FIG. 8 is a timing chart illustrating when the aerosol inhaler 1 performs aerosol generation according to puff actions. First, at a time t1, the aerosol generation request detecting unit 51 detects the aerosol generation request based on the output result of the inhalation sensor 15. After the time t1, at a time t2, the power supply state diagnosis unit 52 acquires an open circuit voltage OCV1 of the power supply 12 measured by the pressure sensor 13.

After acquiring the open circuit voltage OCV1 at the time t2, the power supply state diagnosis unit 52 performs control to close the switch 19 for diagnosing the power supply 12. Here, the time for which when the switch 19 is closed is such a short time that aerosol generation is not performed. In other words, in the period when the switch 19 is closed, current smaller than current when discharging to the load 21 is performed to generate an aerosol flows in the load 21.

As shown in FIG. 8, immediately after the switch 19 is closed, the power-supply voltage of the power supply 12 instantly drops according to the inter-electrode internal resistance of the power supply 12 (the resistance between the electrodes which lithium ions encounter when moving the electrodes). Thereafter, the power-supply voltage of the power supply 12 gradually drops and stabilizes due to the reaction resistance of the power supply 12 (the resistance when lithium ions move in the interfaces between the electrodes and the electrolytic solution).

At a time t3 when dropping of the power-supply voltage attributable to the reaction resistance ends, the power supply state diagnosis unit 52 acquires a closed circuit voltage CCV1 of the power supply 12 measured by the voltage sensor 16. If the closed circuit voltage CCV1 is acquired, the power supply state diagnosis unit 52 performs control to open the switch 19. Thereafter, PWM control on the switch 19 is started by the power control unit 53, and aerosol generation is performed.

The power supply state diagnosis unit 52 calculates the internal resistance of the power supply 12 (the sum of the inter-electrode internal resistance and the reaction resistance) by subtracting the closed circuit voltage CCV1 acquired at the time t3 from the open circuit voltage OCV1 acquired at the time t2, and dividing the result value by the value of current applied to the load 21 in the period after the time t2 when the switch 19 was closed for diagnosing the power supply 12.

Then, in the case where the internal resistance difference between the calculated internal resistance and the internal resistance when the power supply is brand new exceeds the above-mentioned resistance threshold, the power supply state diagnosis unit 52 diagnoses that the power supply 12 is in the deteriorated state; whereas in the case where the internal resistance difference is equal to or smaller than the above-mentioned resistance threshold, the power supply state diagnosis unit diagnoses that the power supply 12 is not in the deteriorated state.

In this third diagnosis process, the output signal of the voltage sensor 16 becomes information which is used to diagnose the state of the power supply 12. Also, in the third diagnosis process, in order to obtain the result of the diagnosis on whether the power supply 12 is in the deteriorated state, a time T1 from the time t2 shown in FIG. 8 to a time t4 when the period when the switch 19 is closed for diagnosing the power supply 12 ends is required. This time T1 is a time shorter than each of the time required to obtain the diagnosis result by the first diagnosis process and the time required to obtain the diagnosis result by the second diagnosis process.

(Fourth Diagnosis Process)

The fourth diagnosis process is a process of diagnosing whether the power supply 12 is in the deteriorated state, based on the temperature of the power supply 12. As deterioration of the power supply 12 progresses, the amount of heat generation of the power supply 12 when charging and discharging are performed due to Joule heat attributable to the deteriorated internal resistance increases. In the fourth diagnosis process, by monitoring the temperature of the power supply 12 corresponding to the amount of heat generation, whether the power supply 12 is in the deteriorated state is diagnosed.

Specifically, at the time t4 which is a timing immediately before aerosol generation in the timing chart shown in FIG. 8, the power supply state diagnosis unit 52 acquires the temperature Temp1 of the power supply 12 measured by the temperature sensor 17. After the time t4, if PWM control is started by the power control unit 53, and the PWM control ends, whereby aerosol generation ends, at a time t5, the power supply state diagnosis unit 52 acquires the temperature Temp1 of the power supply 12 measured by the temperature sensor 17. Then, in the case where a temperature difference obtained by subtracting the temperature Temp1 from a temperature Temp2 exceeds a temperature threshold, the power supply state diagnosis unit 52 diagnoses that the power supply 12 is in the deteriorated state in which deterioration has progressed more than the predetermined state; whereas in the case where the temperature difference is equal to or smaller than the temperature threshold, the power supply state diagnosis unit diagnoses that the power supply 12 is not in the deteriorated state.

In this fourth diagnosis process, the output signal of the temperature sensor 17 becomes information which is used to diagnose the state of the power supply 12. Also, in the fourth diagnosis process, in order to obtain the result of the diagnosis on whether the power supply 12 is in the deteriorated state, a time T3 from the time t4 to the time t5 shown in FIG. 8 is required. This time T3 is a time shorter than each of the time required to obtain the diagnosis result by the first diagnosis process and the time required to obtain the diagnosis result by the second diagnosis process. Also, this time T3 is a time longer than the time T1 required to obtain the diagnosis result by the third diagnosis process.

However, two temperature acquisition timings which are used in the fourth diagnosis process are not limited to the above-mentioned examples. For example, at an arbitrary timing between the time t1 and the time t4 shown in FIG. 8, the temperature Temp1 of the power supply 12 may be acquired.

(Fifth Diagnosis Process)

The fifth diagnosis process is a process of diagnosing whether the power supply 12 is in a broken state, based on change of the power-supply voltage of the power supply 12 before and after aerosol generation. Here, in the broken state of the power supply 12, an internal short circuit attributable to contact between the positive electrode and the negative electrode which occurs in the power supply, and an external short circuit attributable to contact between the positive electrode and the negative electrode by a low-resistance conductor which occurs outside the power supply are included.

If the internal short circuit or the external short circuit occurs, the voltage drop which is the value is obtained by subtracting the power-supply voltage of the power supply 12 after aerosol generation from the power-supply voltage of the power supply 12 before aerosol generation becomes larger than a value corresponding to the amount of discharge used in aerosol generation. In the fifth diagnosis process, by monitoring the voltage drop, whether the power supply 12 is in the broken state is diagnosed.

Specifically, at the time t2 which is a timing before aerosol generation in the timing chart shown in FIG. 8, the power supply state diagnosis unit 52 acquires the open circuit voltage OCV1 of the power supply 12 measured by the temperature sensor 17. After the time t2, PWM control is started by the power control unit 53, and the PWM control ends, whereby aerosol generation ends. Thereafter, if the aerosol generation request is detected again at a time t6 based on the output result of the inhalation sensor 15, after the time t6, at a time t7, the power supply state diagnosis unit 52 acquires an open circuit voltage OCV2 of the power supply 12 measured by the voltage sensor 16.

Then, in the case where the voltage drop caused by the aerosol generation and obtained by subtracting the open circuit voltage OCV2 from the open circuit voltage OCV1 exceeds a drop threshold, the power supply state diagnosis unit 52 diagnoses that the power supply 12 is in the broken state; whereas in the case where the voltage drop is equal to or smaller than the drop threshold, the power supply state diagnosis unit diagnoses that the power supply 12 is not in the broken state. As this drop threshold, for example, a value larger than a value corresponding to the maximum amount of power required to empty (use up) one second cartridge 30 can be set.

In this fifth diagnosis process, the output signal of the voltage sensor 16 becomes information which is used to diagnose the state of the power supply 12. Also, in the fifth diagnosis process, in order to obtain the result of the diagnosis on whether the power supply 12 is in the broken state, the time T2 from the time t2 to the time t7 shown in FIG. 8 is required. This time T2 is a time shorter than each of the time required to obtain the diagnosis result by the first diagnosis process and the time required to obtain the diagnosis result by the second diagnosis process. Also, this time T2 is a time longer than each of the time T1 required to obtain the diagnosis result by the third diagnosis process and the time T3 required to obtain the diagnosis result by the fourth diagnosis process.

However, at the time t3 which is a timing before aerosol generation in the timing chart shown in FIG. 8, the power supply state diagnosis unit 52 may acquire the closed circuit voltage CCV1 of the power supply 12 measured by the temperature sensor 17. Also, after the time t6, at a time t8 in a period when the switch 19 is temporarily opened, the power supply state diagnosis unit may acquire the closed circuit voltage CCV2 of the power supply 12 measured by the pressure sensor 13. Then, the power supply state diagnosis unit may diagnose whether the power supply 12 is in the broken state, based on whether a value obtained by subtracting the closed circuit voltage CCV2 from the closed circuit voltage CCV1 exceeds the drop threshold.

In the case where the internal short circuit has occurred in the power supply 12, the voltage drop attributable to aerosol generation becomes larger as compared to the case where the external short circuit has occurred in the power supply 12. Therefore, by setting the above-mentioned drop threshold to two stages of a first drop threshold and a second drop threshold larger than the first drop threshold, it is possible to determine which of the internal short circuit and the external short circuit has occurred.

For example, the power supply state diagnosis unit 52 diagnoses that the power supply 12 is in a broken state attributable to the internal short circuit, in the case where the voltage drop obtained by subtracting the open circuit voltage OCV1 from the open circuit voltage OCV2 exceeds the second drop threshold, and diagnoses that the power supply 12 is in a broken state attributable to the external short circuit, in the case where the voltage drop exceeds the first drop threshold and is equal to or smaller than the second drop threshold, and diagnoses that the power supply 12 is not in a broken state, in the case where the voltage drop is equal to or smaller than the first drop threshold.

In the aerosol inhaler 1, in the case where the result of any one of the above-described five types of diagnosis processes represents the "deteriorated state" or the "broken state", the notification control unit 54 controls the notifying unit 45 to notify that the power supply 12 has deteriorated, that the power supply 12 is broken, that it is required to perform replacement of the power supply 12, or the like. Also, in the case where the result of any one of the above-described five types of diagnosis processes represents the "deteriorated state" or the "broken state", the MCU 50 controls such that after that, aerosol generation is not performed. Therefore, it is possible to prevent the aerosol inhaler 1 from being used in the state in which the power supply 12 has deteriorated or is broken, and improve the safety of the product.

(Effects of Aerosol Inhaler of Embodiment)

According to the aerosol inhaler 1, it is possible to diagnose the state of the power supply 12 in various aspects by the five types of diagnosis processes. Therefore, it becomes difficult to overlook an event such as deterioration, breakdown, or the like of the power supply 12 which is overlooked in one diagnosis process. Therefore, it is possible to improve the accuracy of diagnosis on the state of the power supply 12, and it is possible to improve the safety of the product.

Also, according to the aerosol inhaler 1, it is possible to diagnose the state of the power supply 12 by the first diagnosis process, the second diagnosis process, the fourth diagnosis process, and the fifth diagnosis process, in which aerosol generation is necessary, and the third diagnosis process in which aerosol generation is unnecessary. Since the diagnosis on the power supply 12 is performed under different conditions, it is possible to improve the accuracy of diagnosis, and improve the safety of the product.

Also, according to the aerosol inhaler 1, it is possible to diagnose the state of the power supply 12 by the fourth diagnosis process and the fifth diagnosis process, in which one time of aerosol generation is necessary, and the first diagnosis process and the second diagnosis process, in which a plurality of times of aerosol generation are necessary. Therefore, it is possible to detect deterioration or breakdown of the power supply 12 which is observable, in a short time, and it is possible to detect both of deterioration and breakdown of the power supply 12 which is observable, in a long time. Therefore, it is possible to improve the accuracy of diagnosis and improve the safety of the product.

Also, according to the aerosol inhaler 1, it is possible to diagnose the state of deterioration of the power supply 12 by a plurality of types of diagnosis processes (the first diagnosis process, the second diagnosis process, the third diagnosis process, and the fourth diagnosis process). Therefore, it becomes difficult to overlook deterioration of the power supply 12 which is overlooked in one diagnosis process. Therefore, it is possible to improve the accuracy of diagnosis on the power supply 12, and it is possible to improve the safety of the product.

Also, according to the aerosol inhaler 1, diagnosis on the state of the power supply 12 is performed based on the outputs of the plurality of sensors (the pressure sensor 13, the voltage sensor 16, and the temperature sensor 17). Therefore, it is possible to enhance the possibility of being able to detect deterioration or breakdown of the power supply 12 even in the case where any one sensor is broken or an error occurs in the output of the sensor.

Also, according to the aerosol inhaler 1, it is possible to diagnose the state of the power supply 12, using the electric physical quantity which is measured by the voltage sensor 16, and the non-electric physical quantities which are measured by the pressure sensor 13 and the temperature sensor 17. Therefore, it is possible to diagnose the state of the power supply 12 in various aspects. Also, it is possible to enhance the possibility of being able to detect deterioration or breakdown of the power supply 12 even in a situation in which it is impossible to successfully acquire an electric physical quantity due to disturbance such as electromagnetic wave noise.

Also, according to the aerosol inhaler 1, it is possible to diagnose the state of the power supply 12 by the plurality of diagnosis processes for detecting changes in the state of the power supply 12 which are caused by different factors, i.e. the first diagnosis process, the second diagnosis process, the third diagnosis process, and the fourth diagnosis process for diagnosing whether the power supply 12 is in the deteriorated state which is caused by a first factor such as repetitive charging and discharging, leaving the power supply in the fully charged state or the discharge cutoff state, or environmental temperature, and the fifth diagnosis process for diagnosing whether the power supply 12 is in the broken state which is caused by a second factor such as foreign matter inclusion, impact, or a short circuit in an external circuit. As described above, diagnosis on the power supply 12 is performed from different perspectives as described above. Therefore, even in the case where the power supply 12 is deteriorated or broken due to various factors, it is possible to detect the deterioration or the breakdown.

Also, according to the aerosol inhaler 1, it is possible to diagnose the state of the power supply 12 by temperature-dependent diagnosis processes (the first diagnosis process, the third diagnosis process, and the fourth diagnosis process) in which the diagnosis results can change according to the temperature of the power supply 12, and temperature-independent diagnosis processes (the second diagnosis process and the fifth diagnosis process) in which the diagnosis results cannot change according to the temperature of the power supply 12.

The cumulative discharge amount which is used in the first diagnosis process to diagnose the state of the power supply 12 can change according to the temperature of the power supply 12. Therefore, the first diagnosis process is a process in which even though the state of deterioration of the power supply 12 is constant, if the temperature of the power supply 12 changes, the diagnosis result can change. In other words, the first diagnosis process is a process which is influenced by the temperature of the power supply 12. However, in the first diagnosis process, it is possible to improve the accuracy of diagnosis by measuring the temperature of the power supply 12 and changing the threshold in view of the measured temperature.

The internal resistance which is used in the third diagnosis process to diagnose the state of the power supply 12 can change according to the temperature of the power supply 12. Therefore, the third diagnosis process is a process in which even though the state of deterioration of the power supply 12 is constant, if the temperature of the power supply 12 changes, the diagnosis result can change. In other words, the third diagnosis process is a process which is influenced by the temperature of the power supply 12. However, in the third diagnosis process, it is possible to improve the accuracy of diagnosis by measuring the temperature of the power supply 12 and changing the resistance threshold in view of the measured temperature.

As for the amount of heat generation which is used in the fourth diagnosis process to diagnose the state of the power supply 12, even though the state of deterioration of the power supply 12 is constant, as the temperature of the power supply 12 rises due to high environmental temperature, the amount of change in the amount of heat generation decreases. Therefore, the fourth diagnosis process is a process in which the diagnosis result can change according to the temperature of the power supply 12. In other words, the fourth diagnosis process is a process which is influenced by the temperature of the power supply 12. However, in the fourth diagnosis process, it is possible to improve the accuracy of diagnosis by measuring the temperature of the power supply 12 and changing the temperature threshold in view of the measured temperature.

The magnitude of the amount of swelling which is used in the second diagnosis process to diagnose the state of the power supply 12 does not change according to the temperature of the power supply 12. In other words, the second diagnosis process is a process in which the diagnosis result cannot change according to the temperature of the power supply 12, in other words, a process which is not influenced by the temperature of the power supply 12.

The magnitude of the voltage drop which is used in the fifth diagnosis process to diagnose the state of the power supply 12 does not change according to the temperature of the power supply 12. In other words, the fifth diagnosis process is a process in which the diagnosis result cannot change according to the temperature of the power supply 12, in other words, a process which is not influenced by the temperature of the power supply 12.

As described above, diagnosis on the power supply 12 is possible by the temperature-dependent diagnosis processes and the temperature-independent diagnosis processes. Therefore, even in the case where the accuracy of diagnosis which is performed by the temperature-dependent diagnosis processes decreases due to the influence of the ambient environment, it is possible to secure the accuracy of diagnosis by the temperature-independent diagnosis processes. Also, even in a situation in which it is impossible to accurately acquire the temperature of the power supply 12, it is possible to secure the accuracy of diagnosis.

Also, according to the aerosol inhaler 1, it is possible to diagnose the state of the power supply 12 by diagnosis processes in which the diagnosis results can change according to the state of charge of the power supply 12 (the first diagnosis process and the fifth diagnosis process) and diagnosis processes in which the diagnosis results cannot change according to the state of charge of the power supply 12 (the second diagnosis process, the third diagnosis process, and the fourth diagnosis process). Therefore, even in the case where the accuracy of diagnosis which is performed by the former diagnosis processes decreases according to the state of discharge of the power supply 12, it is possible to secure the accuracy of diagnosis by the latter diagnosis processes. Also, depending on the state of discharge of the power supply 12, it is possible to secure the accuracy of diagnosis by the former diagnosis processes. Therefore, it becomes possible to diagnose the power supply 12 from various perspectives.

In the first diagnosis process, the cumulative discharge amount in the voltage range before the plateau region is used as a reference for diagnosis. In other words, the first diagnosis process can secure the accuracy of diagnosis only in the case where the state of charge of the power supply 12 is a predetermined state (a state in which the power-supply voltage is in a non-plateau region). In other words, the first diagnosis process can be referred to as being a process which is influenced by the state of charge of the power supply 12.

The voltage drop which is used in the fifth diagnosis process to diagnose the state of the power supply 12 becomes large in the non-plateau regions. In other words, the fifth diagnosis process can be referred to as being a process capable of securing the accuracy of diagnosis only in the case where the state of charge of the power supply 12 is the predetermined state (the state in which the power-supply voltage is in the plateau region), i.e. as being influenced by the state of charge of the power supply 12.

The magnitude of the amount of swelling which is used in the second diagnosis process to diagnose the state of the power supply 12 does not change according to the state of charge of the power supply 12. In other words, the second diagnosis process can be said as being a process which is not influenced by the state of charge of the power supply 12.

The magnitude of the difference between the open circuit voltage OCV and the closed circuit voltage CCV which is used in the third diagnosis process to diagnose the state of the power supply 12 does not change according to the state of charge of the power supply 12. In other words, the third diagnosis process can be referred to as being a process which is not influenced by the state of charge of the power supply 12.

The magnitude of the amount of heat generation which is used in the fourth diagnosis process to diagnose the state of the power supply 12 does not change according to the state of charge of the power supply 12. In other words, the fourth diagnosis process can be referred to as being a process which is not influenced by the state of charge of the power supply 12.

(First Modification of Control on Notification of Power Supply Diagnosis Result)

It is desirable for the notification control unit 54 to control the notifying unit 45 such that the notifying unit operates in different operation modes depending on the case where the result of any one of the first diagnosis process to the fourth diagnosis process of the above-described five types of diagnosis processes represents the "deteriorated state" and the case where the results of two or more of the first diagnosis process to the fourth diagnosis process represent the "deteriorated state".

For example, in the case where the result of any one of the first diagnosis process to the fourth diagnosis process represents the "deteriorated state", the notification control unit 54 controls the notifying unit 45 to notify the user and so on that deterioration has progressed slightly, for example, by turning on a light emitting element in yellow. In this case, the MCU 50 does not stop aerosol generation, and performs aerosol generation if the aerosol generation request is issued.

Meanwhile, in the case where the results of two or more of the first diagnosis process to the fourth diagnosis process represent the "deteriorated state”, the notification control unit 54 controls the notifying unit 45 to notify the user and so on that it is required to replace the power supply 12, for example, by turning on a light emitting element in red. In this case, even if the aerosol generation request is issued, the MCU 50 does not perform aerosol generation.

According to this modification, it is possible to notify the state of deterioration of the power supply 12 in stages. Also, in the case where the result of only one of the first diagnosis process to the fourth diagnosis process represents the “deteriorated state”, since it is possible to keep using the product, it is possible to improve the safety of the product while improving the degree of satisfaction of the user.

(Second Modification of Control on Notification of Power Supply Diagnosis Result)

The notification control unit 54 may control the notifying unit 45, in any one of the case where the result of the fifth diagnosis process of the above-described five types of diagnosis processes represents the “broken state” and the case where the results of two or more of the first diagnosis process to the fourth diagnosis process of the five types of diagnosis processes, to notify that the power supply 12 is broken, that the power supply 12 has deteriorated, that it is required to replace the power supply 12, or the like.

According to this modification, in the case where the result of only one of the first diagnosis process to the fourth diagnosis process represents the deteriorated state, it is possible to keep using the product. Therefore, it is possible to improve the degree of satisfaction of the user.

In the above-described aerosol inhaler 1, the power supply state diagnosis unit 52 may not perform all of the five types of the first diagnosis process to the fifth diagnosis process. For example, the power supply state diagnosis unit 52 may perform two, three, or four diagnosis processes which are selected from the first diagnosis process to the fifth diagnosis process.

However, diagnosis processes which the power supply state diagnosis unit 52 performs are not limited to the first diagnosis process to the fifth diagnosis process. An arbitrary diagnosis process capable of diagnosing the state of the power supply 12 can be used in addition to the first diagnosis process to the fifth diagnosis process, or instead of any one of the first diagnosis process to the fifth diagnosis process. It should be noted that this arbitrary diagnosis process is different from the first diagnosis process to the fifth diagnosis process in the time required to obtain a result or information which is used to obtain a result, it is possible to obtain the above-described effects capable of achieving the object of this application.

In this specification, at least the following inventions (1) to (13) are disclosed. Moreover, although the corresponding constituent elements and the like in the embodiments described above are shown in parentheses, it is not limited thereto.

(1) A power supply unit (the power supply unit 10) for an aerosol inhaler (the aerosol inhaler 1) comprising:

a power supply (the power supply 12) able to discharge power to a load (the load 21) for generating an aerosol from an aerosol source; and a control unit (the MCU 50) configured to perform a plurality of types of processes for diagnosing a state of the power supply, wherein the plurality of types of processes are different in at least one of time which is required to obtain a result of diagnosis and information which is used to obtain a result of diagnosis.

According to (1), it is possible to diagnose the state of the power supply by the plurality of types of processes. Therefore, it becomes difficult to overlook an event such as deterioration or breakdown of the power supply which is overlooked in one process. Therefore, it is possible to improve the accuracy of diagnosis on the state of the power supply, and it is possible to improve the safety of the product.

(2) The power supply unit according to (1), wherein the plurality of types of processes include a process in which aerosol generation is necessary and a process in which aerosol generation is unnecessary.

According to (2), it is possible to diagnose the state of the power supply by the process in which aerosol generation is necessary and the process in which aerosol generation is unnecessary. Therefore, by double checking, for example, by performing diagnosis before aerosol generation and performing diagnosis after the aerosol generation, it is possible to improve the accuracy of diagnosis, and improve the safety of the product.

(3) The power supply unit according to (1), wherein the plurality of types of processes include a process in which one time of aerosol generation is necessary and a process in which a plurality of times of aerosol generation are necessary.

According to (3), it is possible to detect deterioration or breakdown of the power supply which is observable in a short time, and detect both of deterioration and breakdown of the power supply which are observable in a long time. Therefore, it is possible to improve the accuracy of diagnosis and improve the safety of the product.

(4) The power supply unit according to any one of (1) to (3), wherein the plurality of types of processes include a plurality of types of deterioration diagnosis processes of diagnosing whether the power supply has deteriorated.

According to (4), it is possible to diagnose the state of deterioration of the power supply by the plurality of types of deterioration diagnosis processes. Therefore, it becomes difficult to overlook deterioration of the power supply which is overlooked in one deterioration diagnosis process. Therefore, it is possible to improve the accuracy of diagnosis on the power supply, and it is possible to improve the safety of the product.

(5) The power supply unit according to (4), further comprising:

a notifying unit (the notifying unit 45) for performing notification to a user, wherein in a case of diagnosing that the power supply is in a deteriorated state in which deterioration has progressed more than a predetermined state by one deterioration diagnosis process of the plurality of types of deterioration diagnosis processes, the control unit controls the notifying unit in an operation mode different from an operation mode in a case of diagnosing that the power supply is in a deteriorated state by each of two or more deterioration diagnosis processes of the plurality of types of deterioration diagnosis processes, to notify the deteriorated state.

According to (5), notification of the deteriorated state is issued in different operation modes depending on the case where deterioration of the power supply has been detected by one of the plurality of types of deterioration diagnosis processes and the case where deterioration of the power supply has been detected by two or more deterioration diagnosis processes. Therefore, it is possible to appropriately notify the state of deterioration of the power supply to the user.

(6) The power supply unit according to (4), further comprising:

a notifying unit (the notifying unit 45) for performing notification to a user, wherein only in a case of diagnosing that the power supply is in a deteriorated state in which deterioration has progressed more than a predetermined state by at least two deterioration diagnosis processes of the plurality of types of deterioration diagnosis processes, the control unit controls the notifying unit to notify the deteriorated state.

According to (6), in the case where deterioration of the power supply is detected by one of the plurality of types of deterioration diagnosis processes, notification is not issued, and only in the case where deterioration of the power supply is detected by at least two deterioration diagnosis processes, the occurrence of deterioration of the power supply is notified. Therefore, it is possible to appropriately notify the state of deterioration of the power supply to the user.

(7) The power supply unit according to any one of (1) to (6), further comprising:

a plurality of sensors (the pressure sensor 13, the voltage sensor 16, and the temperature sensor 17) configured to output different physical quantities, wherein the plurality of types of processes includes a plurality of processes of performing diagnosis on the state of the power supply based on the different physical quantities which are outputted from the sensors.

According to (7), diagnosis on the state of the power supply is performed based on the outputs of the plurality of sensors. Therefore, it is possible to enhance the possibility of being able to detect deterioration or breakdown of the power supply, even in the case where any one sensor is broken and an error occurs in the output of the sensor.

(8) The power supply unit according to (7), wherein the plurality of sensors includes a first sensor (the pressure sensor 13) configured to detect an electric physical quantity to output a signal, and a second sensor (the pressure sensor 13 or the temperature sensor 17) configured to detect a non-electric physical quantity to output a signal, and the plurality of types of processes include a process of diagnosing the state of the power supply based on the signal which is outputted from the first sensor, and a process of diagnosing the state of the power supply based on the signal which is outputted from the second sensor.

According to (8), it is possible to diagnose the state of the power supply using the electric physical quantity and the non-electric physical quantity. Therefore, it is possible to diagnose the state of the power supply from various perspectives. Also, it is possible to enhance the possibility of being able to detect deterioration or breakdown of the power supply, even in a situation in which it is impossible to successfully acquire the electric physical quantity due to disturbance such as electromagnetic wave noise.

(9) The power supply unit according to any one of (1) to (8), wherein the plurality of types of processes include a plurality of processes for diagnosing change in the state of the power supply which is caused by different factors.

According to (9), diagnosis on the power supply is performed from different perspectives. Therefore, even in the case where the power supply is deteriorated or broken due to various factors, it is possible to detect the deterioration or the breakdown.

(10) The power supply unit according to any one of (1) to (9), wherein the plurality of types of processes include a process which is influenced by temperature of the power supply and a process which is not influenced by temperature of the power supply.

According to (10), diagnosis on the power supply is possible by the temperature-dependent process and the temperature-independent process. Therefore, even in the case where the accuracy of diagnosis which is performed by the temperature-dependent process decreases due to the influence of the ambient environment, it is possible to secure the accuracy of diagnosis by the temperature-independent process. Also, even in a situation in which it is impossible to accurately acquire the temperature of the power supply, it is possible to secure the accuracy of diagnosis.

(11) The power supply unit according to any one of (1) to (10), wherein the plurality of types of processes include a process which is influenced by a state of charge of the power supply and a process which is not influenced by a state of charge of the power supply.

According to (11), diagnosis on the power supply is possible by the process in which the accuracy changes depending on the state of charge of the power supply and the process in which the accuracy is secured regardless of the state of charge of the power supply. Therefore, even in the case where the accuracy of diagnosis which is performed the former process decreases based on the state of discharge of the power supply, it is possible to secure the accuracy of diagnosis by the latter process. Also, depending on the state of discharge of the power supply, it is possible to secure the accuracy of diagnosis by the former process. Therefore, it becomes possible to diagnose the power supply from various perspectives.

(12) A method of diagnosing a state of a power supply of an aerosol inhaler including a power supply able to discharge power to a load for generating an aerosol from an aerosol source, the method comprising:

a control step of performing a plurality of types of processes for diagnosing the state of the power supply, wherein the plurality of types of processes are different in at least one of time which is required to obtain a result of diagnosis and information which is used to obtain a result of diagnosis.

(13) A program for diagnosing a state of a power supply of an aerosol inhaler including a power supply able to discharge power to a load for generating an aerosol from an aerosol source, wherein the program is for making a computer perform a control step of performing a plurality of types of processes for diagnosing the state of the power supply, and the plurality of types of processes are different in at least one of time which is required to obtain a result of diagnosis and information which is used to obtain a result of diagnosis.

According to (1), (12), and (13), it is possible to diagnose the state of the power supply by the plurality of types of processes. Therefore, it becomes difficult to overlook an event such as deterioration or breakdown of the power supply which is overlooked in one process. Therefore, it is possible to improve the accuracy of diagnosis on the state of the power supply, and it is possible to improve the safety of the product. Since it is possible to appropriately grasp the deteriorated state or broken state of the power supply as described above, it is possible to urge the user and so on to replace the power supply at an appropriate timing. Therefore, there is energy saving effect in which it is possible to maximize the period for which it is possible to use the power supply without replacing with a new one.

What is claimed is:

1. A power supply unit for an aerosol inhaler, the power supply unit comprising:

a power supply able to discharge power to a load for generating an aerosol from an aerosol source; and circuitry configured to perform a plurality of types of processes for diagnosing a state of the power supply, wherein the plurality of types of processes are different in at least one of time which is required to obtain a result of diagnosis and information which is used to obtain a result of diagnosis, the plurality of types of processes include a process in which aerosol generation is necessary and a process in which aerosol generation is unnecessary, and wherein the plurality of types of processes include a plurality of types of deterioration diagnosis processes of diagnosing whether the power supply has deteriorated; and wherein in a case of diagnosing that the power supply is in a deteriorated state in which deterioration has progressed more than a predetermined state by one deterioration diagnosis process of the plurality of types of deterioration diagnosis processes, notify the user of the deteriorated state in an operation mode different from an operation mode in a case of diagnosing that the power supply is in a deteriorated state by each of two or more deterioration diagnosis processes of the plurality of types of deterioration diagnosis processes.

2. The power supply unit according to claim 1, further comprising:

a plurality of sensors configured to output different physical quantities, wherein the plurality of types of processes includes a plurality of processes of performing diagnosis on the state of the power supply based on the different physical quantities which are outputted from the sensors.

3. The power supply unit according to claim 2, wherein the plurality of sensors include a first sensor configured to detect an electric physical quantity to output a signal, and a second sensor configured to detect a non-electric physical quantity to output a signal, and the plurality of types of processes include a process of diagnosing the state of the power supply based on the signal which is outputted from the first sensor, and a process of diagnosing the state of the power supply based on the signal which is outputted from the second sensor.

4. The power supply unit according to claim 1, wherein the plurality of types of processes include a plurality of processes for diagnosing change in the state of the power supply which is caused by different factors.

5. The power supply unit according to claim 1, wherein the plurality of types of processes include a process which is influenced by temperature of the power supply and a process which is not influenced by temperature of the power supply.

6. The power supply unit according to claim 1, wherein the plurality of types of processes include a process which is influenced by a state of charge of the power supply and a process which is not influenced by a state of charge of the power supply.

7. A power supply unit for an aerosol inhaler, the power supply unit comprising:

a power supply able to discharge power to a load for generating an aerosol from an aerosol source; and circuitry configured to perform a plurality of types of processes for diagnosing a state of the power supply, wherein the plurality of types of processes are different in at least one of time which is required to obtain a result of diagnosis and information which is used to obtain a result of diagnosis, the plurality of types of processes include a process in which one time of aerosol generation is necessary and a process in which a plurality of times of aerosol generation are necessary, and wherein the plurality of types of processes include a plurality of types of deterioration diagnosis processes of diagnosing whether the power supply has deteriorated; and wherein in a case of diagnosing that the power supply is in a deteriorated state in which deterioration has progressed more than a predetermined state by one deterioration diagnosis process of the plurality of types of deterioration diagnosis processes, notify the user of the deteriorated state in an operation mode different from an operation mode in a case of diagnosing that the power supply is in a deteriorated state by each of two or more deterioration diagnosis processes of the plurality of types of deterioration diagnosis processes.

8. The power supply unit according to claim 7, further comprising:

a plurality of sensors configured to output different physical quantities, wherein the plurality of types of processes includes a plurality of processes of performing diagnosis on the state of the power supply based on the different physical quantities which are outputted from the sensors.

9. The power supply unit according to claim 8, wherein the plurality of sensors include a first sensor configured to detect an electric physical quantity to output a signal, and a second sensor configured to detect a non-electric physical quantity to output a signal, and the plurality of types of processes include a process of diagnosing the state of the power supply based on the signal which is outputted from the first sensor; and a process of diagnosing the state of the power supply based on the signal which is outputted from the second sensor.

10. The power supply unit according to claim 7, wherein the plurality of types of processes include a plurality of processes for diagnosing change in the state of the power supply which is caused by different factors.

11. The power supply unit according to claim 7, wherein the plurality of types of processes include a process which is influenced by temperature of the power supply and a process which is not influenced by temperature of the power supply.

12. The power supply unit according to claim 7, wherein the plurality of types of processes include a process which is influenced by a state of charge of the power supply and a process which is not influenced by a state of charge of the power supply.

13. A power supply unit for an aerosol inhaler, the power supply unit comprising:

a power supply able to discharge power to a load for generating an aerosol from an aerosol source; and circuitry configured to perform a plurality of types of processes for diagnosing a state of the power supply, wherein the plurality of types of processes are different in at least one of time which is required to obtain a result of diagnosis and information which is used to obtain a result of diagnosis, the plurality of types of processes include a process in which aerosol generation is necessary and a process in which aerosol generation is unnecessary, and wherein the plurality of types of processes include a plurality of types of deterioration diagnosis processes of diagnosing whether the power supply has deteriorated; and notify a user of the deteriorated state only in a case of diagnosing that the power supply is in a deteriorated state in which deterioration has progressed more than a predetermined state by at least two deterioration diagnosis processes of the plurality of types of deterioration diagnosis processes.

* * * * *